United States Patent
Yan et al.

(10) Patent No.: US 11,813,059 B2
(45) Date of Patent: Nov. 14, 2023

(54) SENSOR FOR A CONTINUOUS BIOLOGICAL MONITOR HAVING NITRIC OXIDE RELEASING COMPOUND

(71) Applicant: Zense-Life Inc., Carlsbad, CA (US)

(72) Inventors: Qinyi Yan, San Diego, CA (US); Robert James Boock, Carlsbad, CA (US); Jessie Haskamp, San Diego, CA (US); Huashi Zhang, San Juan Capistrano, CA (US)

(73) Assignee: Zense-Life Inc., Carlsbad, CA (US)

( * ) Notice: Subject to any disclaimer, the term of this patent is extended or adjusted under 35 U.S.C. 154(b) by 105 days.

(21) Appl. No.: 17/457,004

(22) Filed: Nov. 30, 2021

(65) Prior Publication Data

US 2023/0165493 A1    Jun. 1, 2023

(51) Int. Cl.
| | |
|---|---|
| *A61B 5/145* | (2006.01) |
| *A61B 5/1486* | (2006.01) |
| *A61B 5/266* | (2021.01) |
| *A61B 5/265* | (2021.01) |
| *A61B 5/268* | (2021.01) |

(52) U.S. Cl.
CPC ........ *A61B 5/14865* (2013.01); *A61B 5/14532* (2013.01); *A61B 5/265* (2021.01); *A61B 5/266* (2021.01); *A61B 5/268* (2021.01); *A61B 2562/125* (2013.01)

(58) Field of Classification Search
CPC ..... A61B 5/14865; A61B 5/268; A61B 5/266; A61B 5/265; A61B 5/14532; A61B 2562/125
See application file for complete search history.

(56) References Cited

U.S. PATENT DOCUMENTS

| 2013/0245412 A1 | 9/2013 | Rong et al. | |
|---|---|---|---|
| 2013/0261537 A1* | 10/2013 | Hofler et al. | C01B 21/24 604/23 |

(Continued)

FOREIGN PATENT DOCUMENTS

KR    101512566 B1    4/2015

OTHER PUBLICATIONS

International Search Report and Written Opinion dated Feb. 7, 2023 for PCT Patent Application No. PCT/IB2022/060404.

(Continued)

*Primary Examiner* — Eric J Messersmith
(74) *Attorney, Agent, or Firm* — MLO, a professional corp.

(57) ABSTRACT

A subcutaneous sensor for use with a continuous glucose monitor includes a reference electrode, a working electrode, and a composition for releasing nitric oxide (NO). The reference electrode includes a reference substrate and an ion limiting layer over the reference substrate. The working electrode includes a conductive substrate, an interference layer over the conductive substrate, an enzyme layer over the interference layer, and a glucose limiting layer. The enzyme layer has an enzyme for reacting with in-vivo glucose in body fluid of a patient. The glucose limiting layer is over the enzyme layer and limits an amount of the in-vivo glucose from the body fluid of the patient that passes to the enzyme layer. The composition for releasing nitric oxide (NO) includes a NO release compound, a hydrophilic material and a hydrophobic material. The composition is on the reference electrode.

20 Claims, 9 Drawing Sheets

(56) References Cited

U.S. PATENT DOCUMENTS

| | | | |
|---|---|---|---|
| 2013/0274574 A1 | 10/2013 | Say et al. | |
| 2017/0135618 A1 | 5/2017 | Brister et al. | |
| 2017/0238852 A1* | 8/2017 | Schoenfisch et al. | ..................... A61B 5/14865 |
| 2018/0271413 A1* | 9/2018 | Chaum et al. | .... A61M 5/14216 |
| 2019/0069820 A1 | 3/2019 | Chen et al. | |
| 2019/0310218 A1 | 10/2019 | Boock et al. | |
| 2019/0331656 A1* | 10/2019 | Chaum et al. | ....... G01N 27/403 |
| 2021/0322555 A1 | 10/2021 | Doxey | |
| 2022/0296867 A1* | 9/2022 | Avula et al. | ........ A61M 31/002 |

OTHER PUBLICATIONS

Koh, A., Lu, Y., & Schoenfisch, M. H. (2013). Fabrication of nitric oxide-releasing porous polyurethane membranes-coated needle-type implantable glucose biosensors. Analytical chemistry, 85(21), 10488-10494. (Year: 2013).*

Schofield, Jonathon Blake. Design and In Vitro Studies of Nitric Oxide Releasing Glucose Sensor Membranes. 2016. https://doi.org/10.17615/wq9a-sq32 (Year: 2016).*

Soto, R. J., Merricks, E. P., Bellinger, D. A., Nichols, T. C., & Schoenfisch, M. H. (2018). Influence of diabetes on the foreign body response to nitric oxide-releasing implants. Biomaterials, 157, 76-85. (Year: 2018).*

Yan et al., Intravascular glucose/lactate sensors prepared with nitric oxide releasing poly(lactide-co-glycolide)-based coatings for enhanced biocompatibility, Biosensors and Bioelectronics 26, Apr. 2011, pps. 4276- 4282.

* cited by examiner

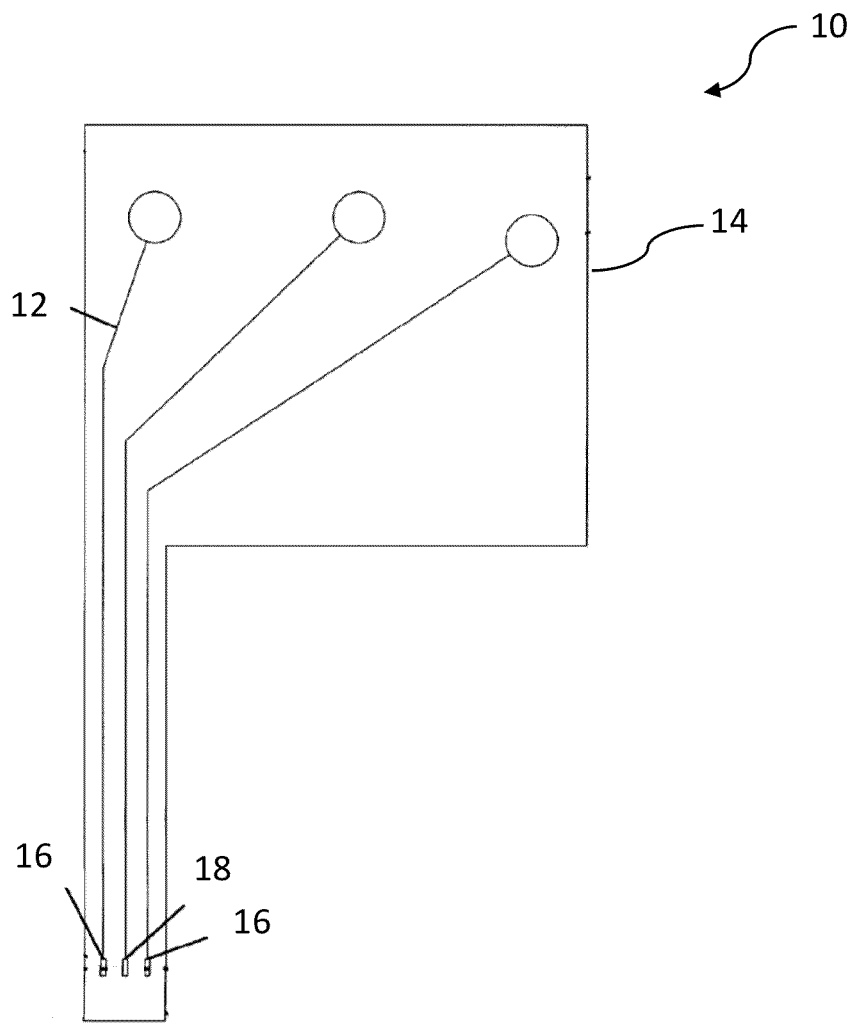
FIG. 1A – Prior Art

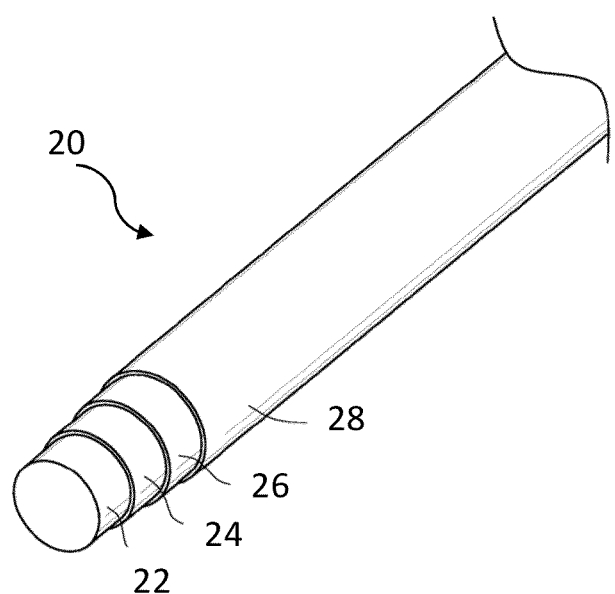
FIG. 1B – Prior Art

SENSOR FOR A CONTINUOUS BIOLOGICAL MONITOR HAVING NITRIC OXIDE RELEASING COMPOUND

BACKGROUND

Monitoring of glucose levels is critical for diabetes patients. Continuous glucose monitoring (CGM) sensors are a type of device in which glucose is measured from fluid sampled in an area just under the skin multiple times a day. CGM devices typically involve a small housing in which the electronics are located and which is adhered to the patient's skin to be worn for a period of time. A small needle within the device delivers the subcutaneous sensor which is often electrochemical.

Glucose readings taken by the sensor can be tracked and analyzed by a monitoring device, such as by scanning the sensor with a customized receiver or by transmitting signals to a smartphone or other device that has an associated software application. Software features that have been included in CGM systems include viewing glucose levels over time, indicating glucose trends, and alerting the patient of high and low glucose levels.

Medical patients often have diseases or conditions that require the measurement and reporting of biological conditions. For example, if a patient has diabetes, it is important that the patient have an accurate understanding of the level of glucose in their system. Traditionally, diabetes patients have monitored their glucose levels by sticking their finger with a small lance, allowing a drop of blood to form, and then dipping a test strip into the blood. The test strip is positioned in a handheld monitor that performs an analysis on the blood and visually reports the measured glucose level to the patient. Based upon this reported level, the patient makes critical health decisions on what food to consume, or how much insulin to inject. Although it would be advantageous for the patient to check glucose levels many times throughout the day, many patients fail to adequately monitor their glucose levels due to the pain and inconvenience. As a result, the patient may eat improperly or inject either too much or too little insulin. Either way, the patient has a reduced quality of life and increased risk of doing permanent damage to their health and body. Diabetes is a devastating disease that if not properly controlled can lead to terrible physiological conditions such as kidney failure, skin ulcers, or bleeding in the eyes and eventually blindness, pain and often the amputation of limbs.

Complicating a patient's glucose monitoring, it is known that blood glucose levels can significantly raise or lower quickly, due to several known and unknown causes. Accordingly, a single glucose measurement provides only a brief snapshot of the instantaneous glucose level in a patient's body. Such a single measurement provides little information about how the patient's use of glucose is changing over time, or how the patient reacts to specific dosages of insulin. Accordingly, even a patient that is adhering to a strict schedule of finger pricking and strip testing, the patient will likely be making incorrect decisions as to diet, exercise, and insulin injection. Of course, this is exacerbated by a patient that is less consistent on their strip testing. To give the patient a more complete understanding of their diabetic condition and to get a better therapeutic result, some diabetic patients are now using continuous glucose monitoring.

The CGM sensor is typically temporarily adhered to the patient's skin with an adhesive pad, and the CGM sensor couples to a small housing in which electronics are located. The CGM sensor typically has a disposable applicator device that uses a small introducer needle to deliver the CGM sensor subcutaneously for the patient. Once the CGM sensor is in place, the applicator is discarded, and the electronics housing is attached to the sensor. Although the electronics housing is reusable and may be used for extended periods, the CGM sensor and applicator need to be replaced often, usually every few days.

It will be understood that, depending upon the patient's specific medical needs, continuous glucose monitoring may be performed at different intervals. For example, some continuous glucose monitors may be set to take multiple readings per minute, whereas in other cases the continuous glucose monitor can be set to take readings every hour or so. It will be understood that a continuous glucose monitor may sense and report glucose readings at different intervals, and the reading rate may change depending on past measurements, time of day, or other criteria.

Electrochemical glucose sensors operate by using electrodes which typically detect an amperometric signal caused by oxidation of enzymes during conversion of glucose to gluconolactone. The amperometric signal can then be correlated to a glucose concentration.

Unfortunately, the useful life of the CGM sensor is time limited, primarily due to the immune system response and body's rejection of the sensor over time. Foreign body response is a typical tissue response to a foreign body within biological tissue. That is, the body may have a foreign body response to the CGM sensor under the skin, and the body causes an inflammatory immune response that is painful. Further, the body's immune system response causes a localized increase in metabolic activity, which artificially decreases the level of glucose near the CGM sensor, resulting in degrading the overall performance of the sensor. The body's immune response begins immediately and becomes acute within about one week. At this point, the CGM sensor needs to be removed and moved to a new location.

SUMMARY

In some embodiments, a subcutaneous sensor for use with a continuous glucose monitor is disclosed. The subcutaneous sensor includes a reference electrode, a working electrode, and a composition for releasing nitric oxide (NO). The reference electrode includes a reference substrate and an ion limiting layer over the reference substrate. The working electrode includes a conductive substrate, an interference layer over the conductive substrate, an enzyme layer over the interference layer, and a glucose limiting layer. The enzyme layer has an enzyme for reacting with in-vivo glucose in body fluid of a patient. The glucose limiting layer is over the enzyme layer and limits an amount of the in-vivo glucose from the body fluid of the patient that passes to the enzyme layer. The composition for releasing NO includes a NO release compound, a hydrophilic material and a hydrophobic material. The composition is on the reference electrode.

In some embodiments, a method of making a subcutaneous sensor for use with a continuous glucose monitor is disclosed. The method includes preparing a composition for releasing NO including mixing a NO release compound, a hydrophilic material, a hydrophobic material, and a solvent to form a composition. The composition is applied to a reference electrode. The composition is cured to form the releasing NO on the reference electrode. The reference electrode is positioned separate from a working electrode.

BRIEF DESCRIPTION OF THE DRAWINGS

Each of the aspects and embodiments of the invention described herein can be used alone or in combination with one another. The aspects and embodiments will now be described with reference to the attached drawings.

FIGS. 1A and 1B show examples of prior art electrochemical sensors.

DETAILED DESCRIPTION

Figure 2A:
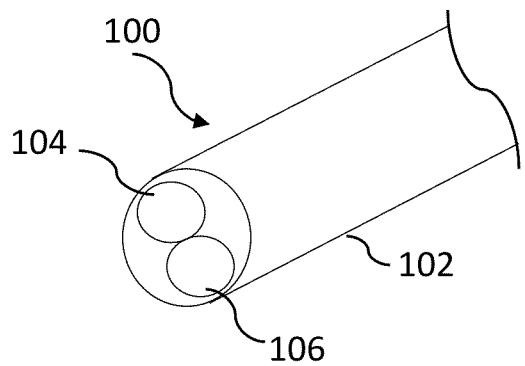
FIGS. 2A and 2B depict an electrochemical sensor, in accordance with some embodiments.

The present disclosure relates to structures and methods for sensors used in a continuous metabolic monitor, such as a continuous glucose monitor (CGM) sensor. In particular, the present devices and methods describe nitric oxide (NO) release compounds for use with a reference electrode and/or working electrode in the CGM sensor. Conventionally, it has been found that doping the CGM sensor with a NO release compound can extend the time of the in-vivo CGM sensor before a foreign body response occurs. However, the presence of NO that has been released from the CGM sensor may interfere with proper generation of the electrical signal indicative of the level of glucose in the fluid of the body of the patient. Accordingly, the NO release compound and the resulting NO may interfere with the accuracy and sensitivity of the CGM sensor.

The embodiments presented herein improve the performance of in-vivo continuous glucose monitoring devices by allowing the sensor to be comfortably worn in the body such as in-vivo use, for extended periods of time without rejection by the body's immune system. It will be understood that cost reduction may be obtained by increasing the length of time between sensor replacements in-vivo for a patient. By decreasing the cost of sensors for continuous monitoring, more patients benefit from the increased quality of life and enhanced therapeutic effect of continuous monitoring.

Electrochemical sensors operate by using electrodes which typically detect an amperometric signal caused by oxidation of enzymes during conversion of glucose to gluconolactone. The amperometric signal can then be correlated to a glucose concentration. Two-electrode (also referred to as two-pole) designs use a working electrode and a reference electrode, where the reference electrode provides a reference against which the working electrode is biased. The reference electrodes essentially complete the electron flow in the electrochemical circuit. Three-electrode (or three-pole) designs have a working electrode, a reference electrode and a counter electrode. The counter electrode replenishes ionic loss at the reference electrode and is part of an ionic circuit.

Most electrochemical sensor designs are either planar (flat substrate) or wire-based. Planar types are more amenable to use with three-pole electrochemical designs since simple wire traces and small electrodes can be easily constructed. However, planar types have deficiencies regarding physiology since a planar substrate has some directionality and also has sharp edges due to its geometry, which leads to a more aggressive biologic response to the device. Wire-based systems result in better physiological responses from the patient than planar systems due to the smooth nature of their geometry but have been mostly confined to a single wire for ease of insertion through an insertion needle. This single wire constraint due to the space limitations of needle-based sensor delivery typically limits the designs to two-pole electrochemical designs.

Prior art electrochemical sensors typically have a sensor design with a single wire so that the working electrode and the reference electrode are integral and part of the same substrate or same wire. In contrast, the present embodiments have a sensor design with two separate wires. A first wire is the working electrode and a second wire is the reference electrode, or the second wire is a combination of the reference electrode and a counter electrode. The working electrode is separate from the reference electrode, and the working electrode and the reference electrode may be arranged side-by-side.

FIGS. 1A and 1B show examples of prior art electrochemical sensors. FIG. 1A depicts a prior art sensor 10 having a design of conductive traces 12 on a substrate 14. Prior art sensor 10 includes the substrate 14, a recessed channel formed in a surface of the substrate 14, and a conductive material disposed in the recessed channel. The conductive material forms a working electrode 16 and two working electrodes 16 are shown. The sensor may also include at least one counter electrode 18 (or counter/reference electrode) and/or at least one reference electrode (not shown). The counter electrode 18 and/or reference electrode may be formed on the same substrate 14 as the working electrode 16 or may be separate units. The counter electrode 18 and/or reference electrode may or may be not be implanted in the patient. FIG. 1B depicts a prior art sensor 20 having a design of coaxial layers on the same wire or substrate. Prior art sensor 20 includes an elongated conductive body with a core 22 and a first layer 24 which includes a working electrode, and at least partially surrounds the core 22. A second layer 26 is comprised of an insulating material and disposed on the first layer 24 such that the working electrode is exposed via a window. A third layer 28 comprises a reference electrode.

Figure 2B:
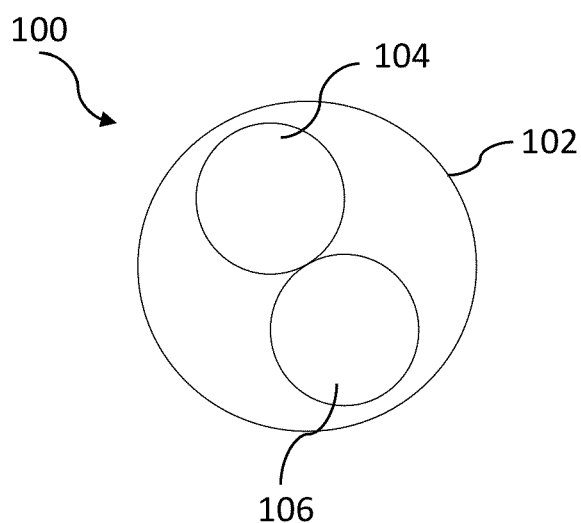
Figure 3A:
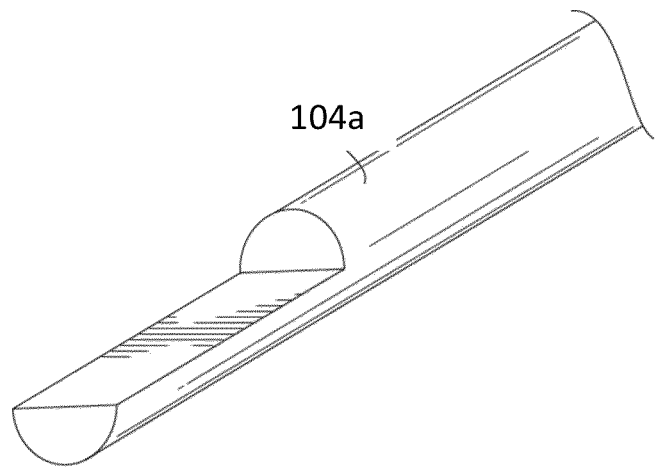
FIGS. 3A and 3B illustrate a one-sided working electrode and a two-sided working electrode, in accordance with some embodiments.
Figure 3B:
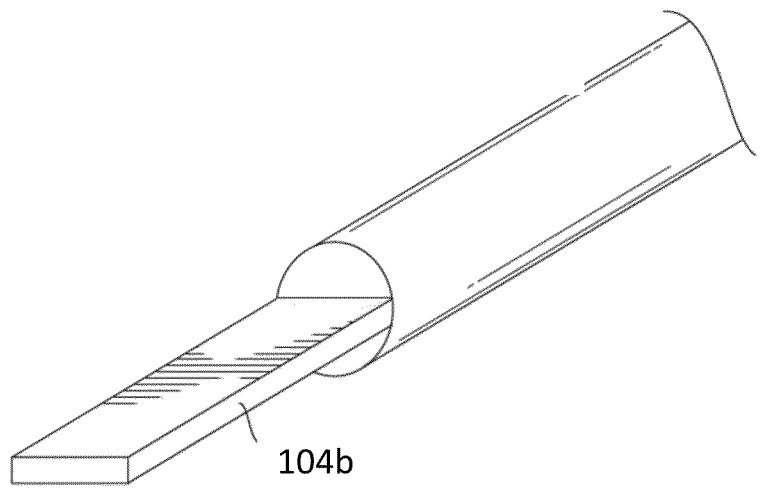

FIGS. 2A and 2B depict an electrochemical sensor, in accordance with some embodiments. The electrochemical sensor 100 may be a continuous glucose monitoring sensor 100. In some embodiments, a two-pole system or two wire system in a small diameter insertion needle 102 is used. For example, a working electrode 104 is one of the poles/wires and a reference electrode 106 is the other pole/wire within the needle 102. The working electrode 104 may be fabricated by creating a flat portion on a wire. FIGS. 3A and 3B illustrate a one-sided working electrode 104a and a two-sided working electrode 104b, in accordance with some embodiments. The one-sided working electrode 104a or the two-sided working electrode 104b may be used in sensor 100. The one-sided working electrode 104a has a semicircular cross-section where half of the wire's cross-sectional area has been removed. Other partial fractions of the wire may be utilized to form the flat surface electrodes by defining by a chord across a circular cross-section of the wire so that the cross-section of the wire may be 30% to 70% of the full wire. The two-sided working electrode 104b has a rectangular cross-section where portions of the wire above and below the flat portion have been removed. The portions removed may be equal or one portion —either the top portion or the bottom portion — may be larger than the other. The flat portion(s) of working electrode 104a or 104b may be used to support an electrochemical element which is the reactive component that senses glucose in the fluid of the patient when the sensor 100 is inserted into the patient, and the wire is the sensor wire for the working electrode in a plurality of sensor wires.

Figure 4:
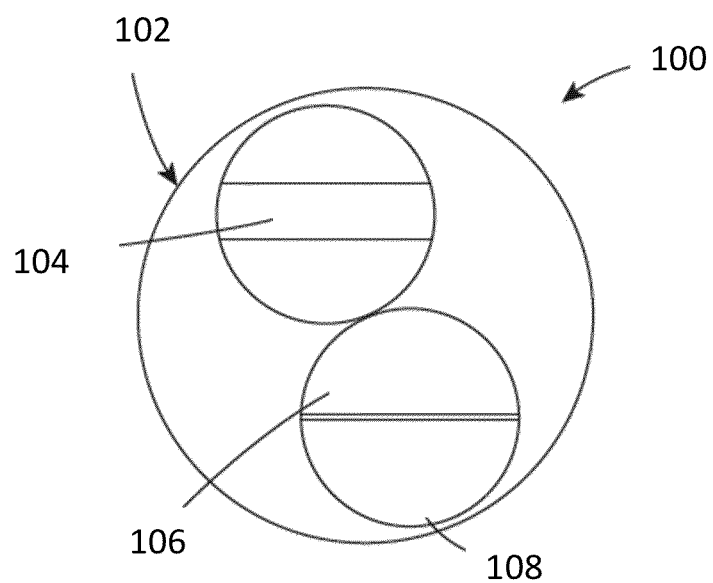
FIG. 4 illustrates a three-pole system for the continuous glucose monitoring sensor, in accordance with some embodiments.

In some embodiments, a three-pole system for the sensor 100 may be used. FIG. 4 illustrates a three-pole system for the continuous glucose monitoring sensor 100, in accordance with some embodiments. In this embodiment, a portion of a wire such as a half-wire is provided for the reference electrode 106. The wire is a sensor wire for the reference electrode 106 in a plurality of sensor wires. Likewise, a portion of a wire such as a half-wire is provided for a counter electrode 108 and is a sensor wire for the counter electrode 108 in the plurality of sensor wires. The sensor wire for the reference electrode 106 and the sensor wire for the counter electrode 108 each have a flat surface across approximately its diameter such that the wires have semicircular cross-sections. In some embodiments, the flat surface of the reference electrode 106 and the flat surface of the counter electrode 108 face toward each other.

Each half-wire electrode, such as the reference electrode 106 and the counter electrode 108, may have an 82% of the surface area of a full wire having the same diameter, while still allowing the reference electrode 106 and counter electrode 108 assembly to fit within a small diameter insertion needle 102 for insertion under the skin. In other words, the split-wire configuration enables the reference electrode 106 and the counter electrode 108 to provide nearly the same surface area as two full wire electrodes, but only occupy the space of one wire within the insertion needle 102 instead of two full wires. Although half-wires are depicted for the reference electrode 106 and counter electrode 108 — where each wire has been split along its diameter along a length of the wire — other partial fractions of the wire may be utilized to form the flat surface electrodes.

Diameters of each of the plurality of sensor wires used for the reference electrode 106, counter electrode 108 or working electrode 104, 104a and 104b may be, for example, from 0.002 inches to 0.007 inches while typical insertion needles may have an internal diameter of 0.16 inches to 0.21 inches or 25 to 27 gauge. The length or surface area of the electrode portions themselves can be tailored according to the desired sensor sensitivity and required design specifications.

Figure 5:
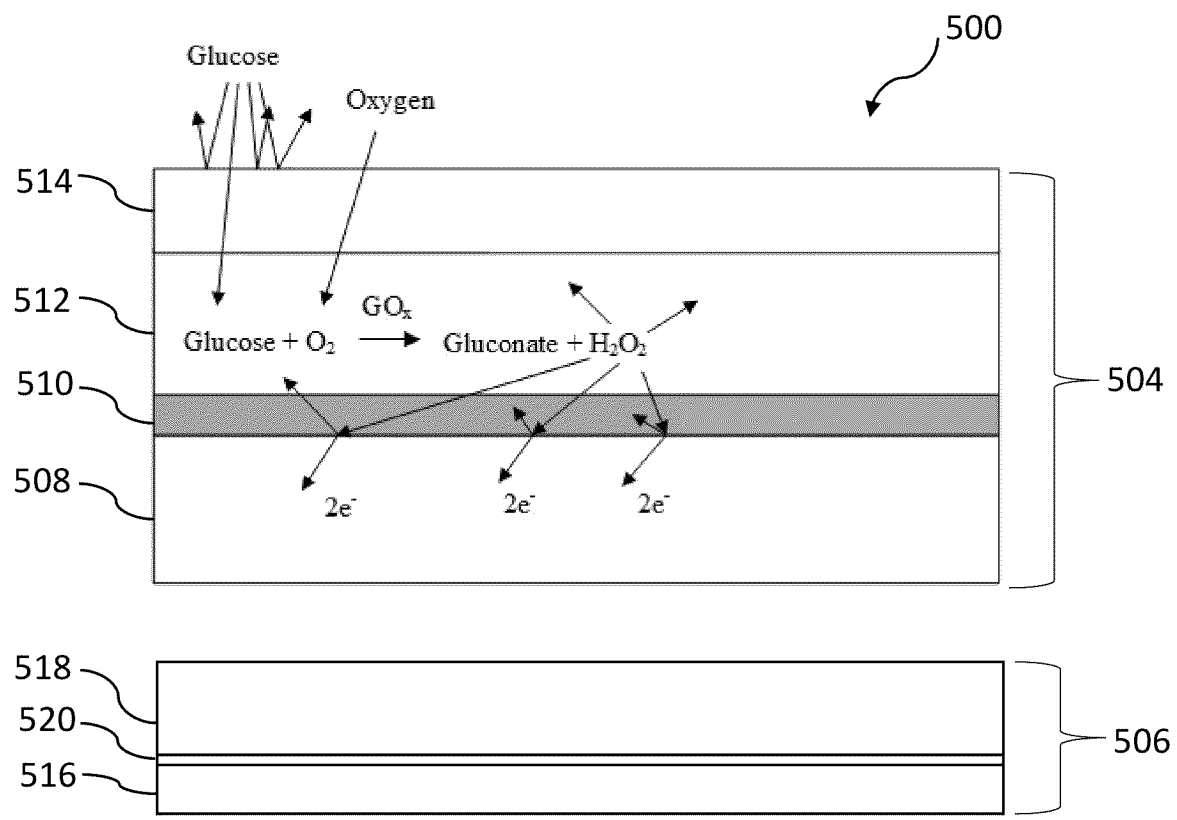
FIG. 5 is a not-to-scale, longitudinal cross-sectional diagram of a working electrode and a reference electrode of a sensor, in accordance with some embodiments.

FIG. 5 is a not-to-scale, longitudinal cross-sectional diagram of a working electrode and a reference electrode of a sensor, in accordance with some embodiments. A sensor 500 for a continuous biological monitor has a working electrode 504 which cooperates with a reference electrode 506 to provide an electrochemical reaction that can be used to determine glucose levels in a fluid of a patient, such as blood or interstitial fluid. Although the sensor 500 is illustrated with one working electrode 504 and one reference electrode 506, it will be understood that some alternative sensors may use multiple working electrodes, multiple reference electrodes, and counter electrodes. It will also be understood that sensor 500 may have different physical relationships between the working electrode 504 and the reference electrode 506. For example, the working electrode 504 and the reference electrode 506 may be arranged in layers, spiraled, or side-by-side. It will be understood that many other physical arrangements may be consistent with the disclosure herein.

The working electrode 504 comprises a conductive substrate 508, an interference membrane 510, an enzyme membrane 512 and a glucose limiting layer 514. The working electrode 504 has a conductive portion, which is illustrated for sensor 500 as conductive wire 508. The conductive wire 508 can be for example, solid platinum, a platinum coating on a less expensive metal or plastic, or a conductive carbon compound coating on a plastic substrate. It will be understood that other electron conductors may be used consistent with this disclosure. As with prior art working electrodes, working electrode 504 has the glucose limiting layer 514, which may be used to limit contaminations and the amount of glucose that is received into the enzyme membrane 512.

The enzyme membrane 512 comprises an enzyme for reacting with in-vivo glucose in body fluid of a patient. In operation, the glucose limiting layer 514 substantially limits the amount of glucose that can reach the enzyme membrane 512, for example only allowing about 1 of 1000 glucose molecules to pass. By strictly limiting the amount of glucose that can reach the enzyme membrane 512, linearity of the overall response is improved. The glucose limiting layer 514 also permits oxygen to travel to the enzyme membrane 512. The key chemical processes for glucose detection occur within the enzyme membrane 512. Typically, the enzyme membrane 512 has one or more glucose oxidase enzymes (GOx) dispersed within the enzyme membrane 512. When a molecule of glucose and a molecule of oxygen ($O_2$) are combined in the presence of the glucose oxidase, a molecule of gluconate and a molecule of hydrogen peroxide ($H_2O_2$) are formed. The hydrogen peroxide then generally disperses both within the enzyme membrane 512 and into the interference membrane 510.

The interference membrane 510 (also known as interference layer) is layered between the conductive wire 508 and the enzyme membrane 512 in the working electrode 504. As will be discussed in more detail below, the interference membrane 510 can be uniquely formulated to have a more precise regulation, compared to conventional insulating layers, of the level of hydrogen peroxide molecules that are enabled to pass from the enzyme membrane layer 512 to a more expansive surface area of the conductive wire 508. The interference membrane 510 may be electrodeposited onto the conductive wire 508 in a very consistent and conformal way, thus reducing manufacturing costs as well as providing a more controllable and repeatable layer formation. The interference membrane 510 is nonconducting of electrons, but will pass negative ions at a preselected rate. Further, the interference membrane 510 may be formulated to be permselective for particular molecules. In one example, the interference membrane 510 is formulated and deposited in a way to restrict the passage of larger molecules, which may act as contaminants to degrade the conductive wire 508, or that may interfere with the electrical detection and transmission processes.

Interference membrane 510 is a solid coating surrounding the conductive wire 508. Accordingly, the interference membrane 510 may be coated or deposited over the conductive wire 508 in a way that has a predictable and consistent passage of hydrogen peroxide. Further, the allowable area of interaction between the hydrogen peroxide and the surface of the conductive wire 508 is dramatically increased, as the interaction may occur anyplace along the conductive wire 508 instead of only in a window area that has been exposed through an insulating layer as in conventional sensors. In this way, the interference membrane 510 enables an increased level of interaction between the hydrogen peroxide molecules in the surface of the conductive wire 508 such that the production of electrons is substantially amplified over prior art working electrodes. In this way, the interference membrane 510 enables the sensor 500 to operate at a higher electron current, reducing the sensor's susceptibility to noise and interference from contaminants, and further enabling the use of less sophisticated and less precise electronics in the housing. In one example, the ability to operate at a higher electron flow allows the sensor's electronics to use more standard operational amplifiers, rather than the expensive precision operational amplifiers required for prior art sensor systems. The resulting improved signal-to-noise ratio enables simplified filtering as well as streamlined calibration.

In some embodiments, the interference membrane 510 is nonconductive of electrons, but is conductive of ions. In some embodiments, an effective interference membrane 510 may be constructed using, for example, poly-ortho-aminophenol (POAP, or poly(o-aminophenol)), polypyrrole, polyaniline, and/or poly(phenylenediamine). For example, a polymer made of monomers selected from aminophenols, aniline, phenylenediamine, pyrrole or combinations thereof may be used in interference membrane 510. In a specific example, the interference membrane may include pyrrole and phenylenediamine. The monomer(s) may be deposited onto the conductive wire 508 (e.g., platinum or platinum-coated) at a thickness that can be precisely controlled to enable a predictable level of hydrogen peroxide to pass through the interference membrane 510 to the platinum of the conductive wire 508. Further, the pH level and/or a salt concentration of the monomer solution may be adjusted to set a desirable permselectivity for the interference membrane 510. For example, the pH and/or salt concentration may be advantageously adjusted to significantly block the passage of larger molecules such as acetaminophen, to reduce contaminants that can reach the conductive wire 508 and skew the electrical signal results. It will be understood that other materials may be used. For example, the interference membrane 510 may include a polymer that has been electropolymerized from: aniline, naphthol, phenylenediamine, 2-aminophenol, 3-aminophenol, 4-aminophenol, m-phenylenediamine, o-phenylenediamine, p-phenylenediamine, pyrrole, derivatized pyrrole, aminophenylboronic acid, thiophene, porphyrin, phenol, or thiophenol or blends thereof.

The sensor 500 has a reference electrode 506 separate from working electrode 504. In this way, the manufacture of the working electrode 504 is simplified and can be performed with a consistency that contributes to dramatically improved stability and performance. The reference electrode 506 comprises a reference substrate which is illustrated as reference wire 516, and an ion limiting layer 518. A paste 520 comprising silver/silver chloride (Ag/AgCl) or iridium oxide may be applied to the reference wire 516 of the reference electrode 506. The ion limiting layer 518 may be over the paste 520. The application of the ion limiting layer 518 over the paste 520 desirably controls the electrical current sensitivity of the overall sensor 500 by controlling the flow of ions from the paste 520. In this way, current sensitivity may be advantageously controlled and defined. As will be understood, this can also act as a secondary method to control sensor sensitivity by controlling the chloride release from the reference electrode 506. In some embodiments, the ion limiting layer 518 of the reference electrode 506 may be selected from polyurethane, cellulosic, polyvinyl chloride (PVC) or combinations thereof.

The sensor 500 incorporates a composition for releasing NO in one or more layers. The composition comprises a NO release compound, a hydrophilic material, and a hydrophobic material. In some embodiments, the NO release compound is selected from S-nitrosothiol, NONOate, L-arginine, nitrovasodilator, or combinations thereof. The S-nitrosothiol family generally takes the following structure, with R denoting an organic group:

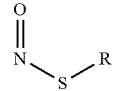

The NONOate family generally takes the following structure:

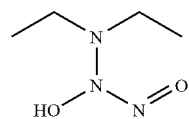

Some examples of compounds in the S-nitrosothiol family are S-nitroso-N-acetylpenicillamine (SNAP) and S-nitrosoglutathione (GSNO). Some examples of compounds in the NONOate family are 1,1-diethyl-2-hydroxy-2-nitrosohydrazine and diethylamine dinitric oxide. An example of a compound in the nitrovasodilator family is nitroglycerin. Herein, SNAP is used in the examples for the NO release compound, but it will be understood that other compounds in the S-nitrosothiol family, NONOate family, L-arginine, nitrovasodilator or combinations thereof, may be used as the NO release compound.

In some embodiments, the hydrophilic material in the composition for releasing NO is selected from polyvinylpyrrolidone (PVP), polyvinyl alcohol, polyacrylic acid, polyethylene oxide (PEO), silane-PEO (Si-PEO), PEO compounds, polyethylene glycol (PEG), or combinations thereof. The PVP may have a molecular weight in the range of 50,000 to 2,000,000 atomic units. Other compositions of PVP having other molecular weights may also be used. It is desirable to identify a hydrophilic material that has a relatively high molecular weight, for example, a molecular weight of 1 to 5 million. It has been found in accordance with embodiments of the present disclosure that hydrophilic material with a molecular weight of 1 to 3 million is particularly effective. As understood, the molecular weight of a polymer is the sum of the atomic weights of all the atoms in the molecule. Accordingly, the selected hydrophilic material is typically a significantly large polymer. Further, the hydrophilic body material is selected to be readily dispensable in standard manufacturing processes, and to have the ability to form strong hydrogen bonds. Although in some embodiments the hydrophilic material has a relatively high molecular weight, is readily dispensable, and has strong hydrogen capability, other characteristics may become important depending upon the specific application.

In some embodiments, the hydrophobic material in the composition for releasing NO is selected from polyurethane, cellulosic, polyvinyl chloride (PVC), silicone or combinations thereof. The hydrophobic material is selected based on a desirable biocompatibility, as well as a ratio between hard and soft segments. Generally, hydrophobic materials are formed of segments of small monomers which are cross-linked to much larger polymer sections. A higher proportion of soft segments allows the hydrophobic bond material to have a higher degree of interaction with a solvent and hydrophilic material; however, the higher ratio of soft segments also decreases the hydrophobic characteristic of the material, as the small segments tend to be hydrophilic. As to the hard segments, a higher ratio of hard segments provides for a stronger physical characteristic, which is often measured as a Shore hardness using a durometer. In this way, a hydrophobic material may be selected that has an appropriate level of interaction with the solvent and hydrophilic materials, as well as having sufficient hardness to act effectively as a protective coating. In some embodiments, polyurethane may be used as a hydrophobic bond material, with the desired characteristics of both providing sufficient hardness, as well as desirable interaction with the hydrophilic bond material (e.g., PVP) and the selected solvent. It will also be appreciated that other types of hydrophobic materials may be selected according to application-specific needs.

The composition may further include a solvent. The solvent is selected from tetrahydrofuran (THF), dimethylformamide (DMF), dimethylacetamide (DMAc), ethanol, or combinations thereof. A solvent is selected that is polar, binary, and sufficiently volatile for the curing of the composition. First, the solvent should have sufficiently strong polar characteristics to assist in properly aligning the hydrophilic and hydrophobic bonding materials. Second, as the solvent must dissolve both the hydrophilic and the hydrophobic material, the solvent should be selected for advantageous dissolving characteristics for each of the selected bonding materials. It will be understood that there are ternary solvents that can be substituted. Finally, the volatility of the solvent should be selected to support the desired cure characteristics. For example, some applications may need to be completed in a short period of time, thus requiring a high evaporative rate solvent. In other cases, less volatile solvents may be substituted. It will be understood that other compounds may be used that can provide the desirable characteristics of the solvent.

In prior art sensors, the composition for releasing NO is a conventional part of or on the working electrode. In this configuration, it is known that the NO release compound and the resulting NO may cause an interference with the accuracy and sensitivity of the sensor. In contrast, in embodiments herein, the composition for releasing NO is on the reference electrode. The ion limiting layer helps control the chloride ion released from the reference electrode. By incorporating the composition on the reference electrode, the ionic transport is limited and can be tailored and controlled. In this way, the composition for releasing NO is an ionic limitation system to help control the release of chlorine from the Ag/AgCl reaction which completes the electrochemical reaction between the working electrode and the reference electrode.

When the NO releasing compound is on the working electrode as in conventional sensors, there is a risk of a cross reaction of the NO releasing compound with the working reactions of the working electrode. For example, in the working electrode, the enzymatic reaction creates hydrogen peroxide, and the hydrogen peroxide diffuses to the wire surface where it reacts and forms a current. It is problematic having the NO releasing compound near this reaction, such as when on the working electrode, because the NO releasing compound has the potential to scavenge the hydrogen peroxide by reacting directly with it and thereby creating nitrates and other deleterious compounds in the area. The NO releasing compound may also damage the enzyme directly since the NO releasing compound is a free radical compound and very reactive. The NO molecules are very small and freely diffusible across the layers of the working electrode. This cross reaction results in an interference signal of the sensor affecting the current and proper generation of the electrical signal indicative of the level of glucose in the fluid of the body of the patient. To minimize this effect, the NO releasing compound may be moved several radiuses away from the point of this reaction. Unfortunately, when the NO releasing compound is moved, the NO releasing compound is too far away, and the benefits of the NO releasing compound are not realized.

In the present disclosure, there are two wires — one for the working electrode and the other for the reference electrode — and the NO releasing compound can be applied to the reference wire instead of the working electrode. This locates the NO releasing compound a few diffusion radiuses away from the working electrode reactions and releases the NO to the cells more predominantly. In this way, the NO releasing compound is far from the working electrode and does not cross the restrictive membranes of the working electrode to directly impact the performance of the sensor such as causing an interference signal.

The composition for releasing NO may be applied to the reference electrode 506 in several ways. In some embodiments, the composition for releasing NO is part of the ion limiting layer 518 of the reference electrode 506. For example, the ion limiting layer 518 may comprise polyurethane. The polyurethane may be mixed with the components of the composition such as the NO release compound, the hydrophilic material, and the hydrophobic material to form the ion limiting layer 518. In some embodiments, the composition for releasing NO may be mixed with the paste 520 so the composition for releasing NO is part of the paste 520 of the reference electrode 50. In some embodiments, the composition for releasing NO may be located between the paste 520 and the ion limiting layer 518.

Figure 6:
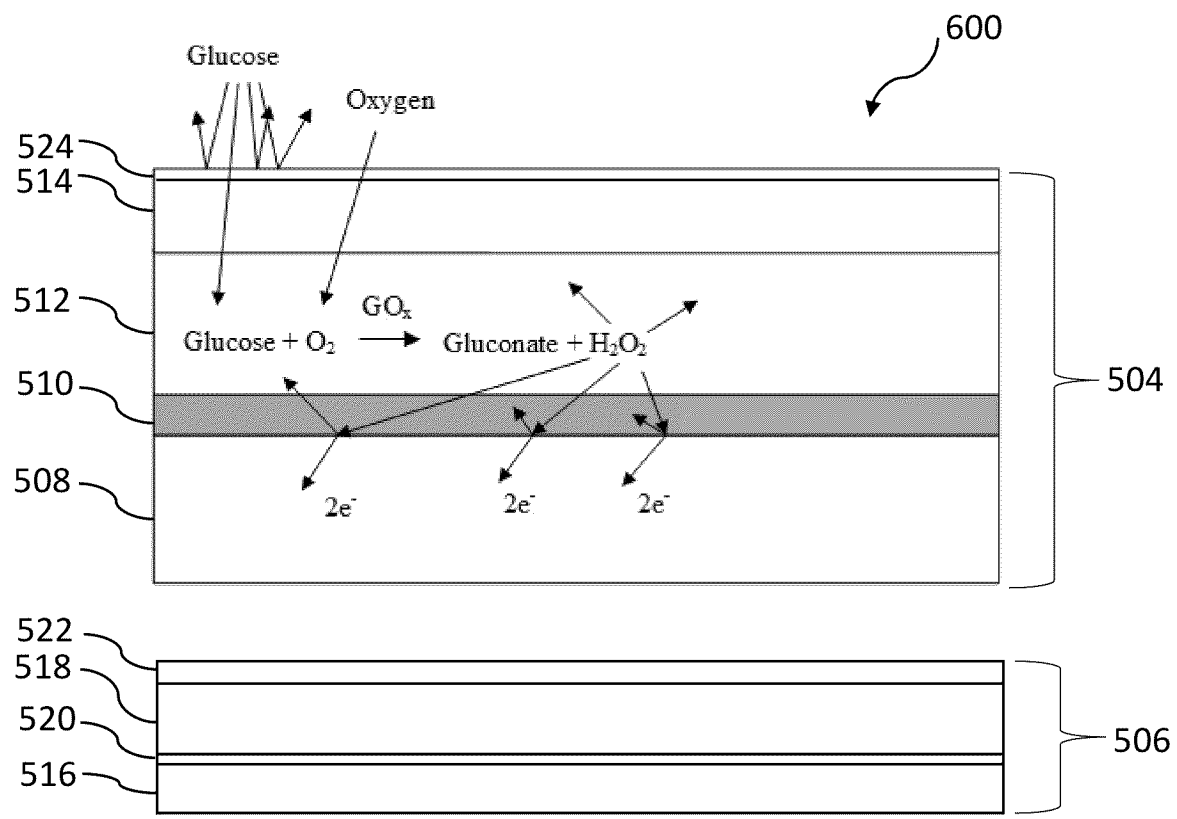
FIG. 6 is a not-to-scale, longitudinal cross-sectional diagram of a working electrode and a reference electrode of a sensor, in accordance with some embodiments.

FIG. 6 is a not-to-scale, longitudinal cross-sectional diagram of a working electrode and a reference electrode of a sensor, in accordance with some embodiments. A sensor 600 is a continuous biological monitor having a working electrode 504 which cooperates with a reference electrode 506. Sensor 600 is similar to the sensor 500 as described herein and will not be described in detail. Sensor 600 includes a reference outer layer 522 over the ion limiting layer 518 of the reference electrode 506, and a working outer layer 524 over the glucose limiting layer 514 of the working electrode 504.

In some embodiments, the composition for releasing NO forms the reference outer layer 522 over the ion limiting layer 518 of the reference electrode 506. The reference outer layer 522 acts as an outer coating for the reference electrode 506 to facilitate a longer usable life for the sensor 500 before the sensor must be moved to a different location on the patient's body due to a foreign body response. The use of the reference outer layer 522 was shown in accordance with the present disclosure to have an exceptional ability to reject the typical interference caused by the presence of released NO. It was observed that resistance to the foreign body response, as well as electrical interference rejection, can be increased with the use of composition for releasing NO on the reference electrode 506.

With reference to the reference electrode 506, the composition for releasing NO may be part of the ion limiting layer 518, part of the paste 520, between the paste 520 and the ion limiting layer 518 or it may form a reference outer layer 522 over the ion limiting layer 518. It will be appreciated that any combination of these may be used. For example, the composition for releasing NO may be part of the ion limiting layer 518 and over the ion limiting layer 518 forming the reference outer layer 522. In another example, the composition for releasing NO may be between the paste 520 and the ion limiting layer 518 and may form a reference outer layer 522 over the ion limiting layer 518. It will be appreciated that the composition in the different locations of the reference electrode 506 may have the same formulation or may have different formulations from one another.

In conjunction with the reference electrode 506 having the composition for releasing the NO, the working electrode 504 may also incorporate the composition for releasing the NO. The composition on the working electrode 504 may have the same formulation as the composition on the reference electrode 506 but may have a different concentration of the composition. For example, the composition on the working electrode 504 may have a reduced concentration being less reactive than the composition on the reference electrode 506. This reduces the detrimental effects of NO on the working electrode seen in the prior art. For example, in some embodiments, when the working electrode 504 has the composition for releasing the NO, it may have 25% of the amount of composition of the amount of composition applied on the reference electrode 506.

Referring to FIG. 5, in some embodiments, the glucose limiting layer 514 of the working electrode 504 may further include the composition for releasing the NO as part as the glucose limiting layer 514. For example, the NO release compound may be SNAP, the hydrophilic material may be PVP, and the hydrophobic material may be polyurethane. These materials along with a solvent, are mixed into the glucose limiting layer 514. Referring to FIG. 6, in some embodiments, the composition for releasing the NO forms the working outer layer 524 over the glucose limiting layer 514 of the working electrode 504. In some embodiments, the working electrode 504 may have the NO release compound as part of the glucose limiting layer 514 and as a working outer layer 524 over the glucose limiting layer 514. It will be understood that sensor 500 and sensor 600 may have the NO release compound on the reference electrode 506 only or on the reference electrode 506 and the working electrode 504.

Figure 7:
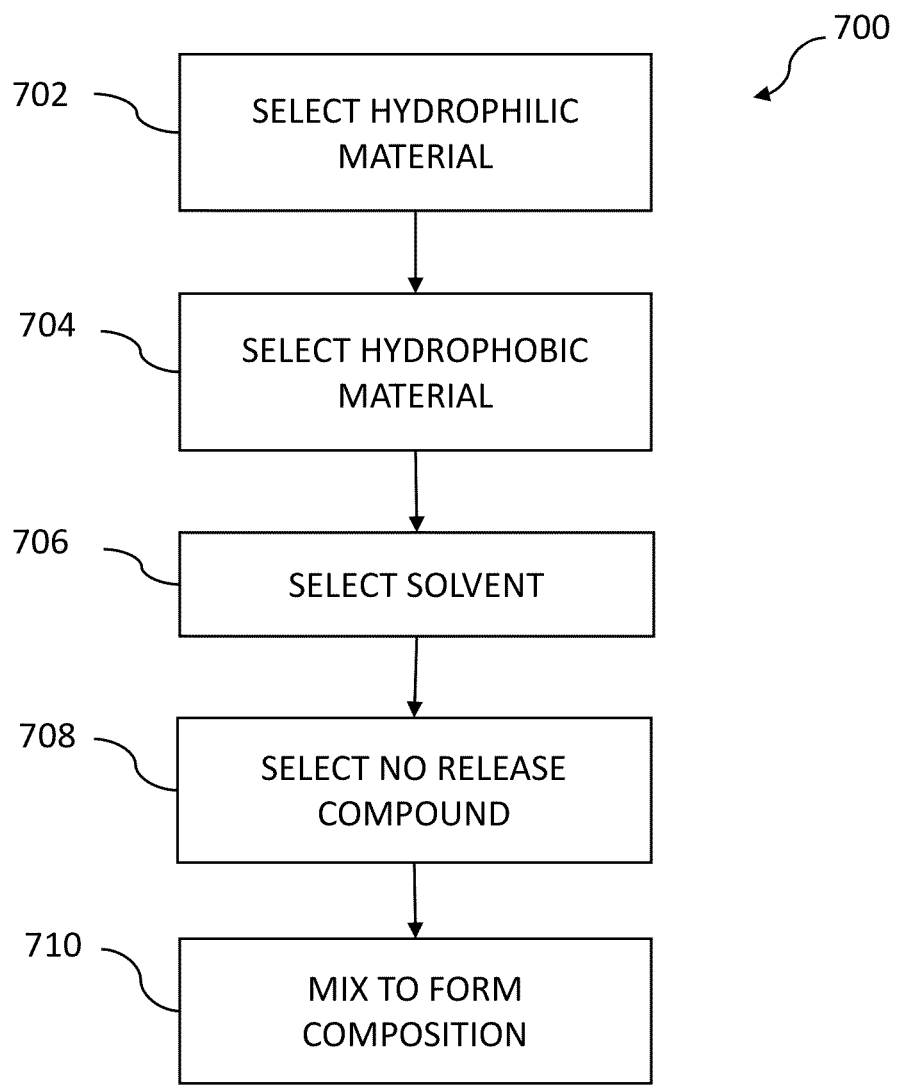
FIG. 7 is a flowchart of a method for making a composition for releasing NO, in accordance with some embodiments.

FIG. 7 is a flowchart of a method 700 for making a composition for releasing NO, in accordance with some embodiments. The method 700 starts at block 702 where a hydrophilic material is selected. The hydrophilic material is selected from polyvinylpyrrolidone (PVP), polyvinyl alcohol, polyacrylic acid, polyethylene oxide (PEO), silane-PEO (Si-PEO), PEO compounds, polyethylene glycol (PEG), or combinations thereof. In an example, PVP with a molecular weight between 50,000 and 2,000,000 atomic mass units is chosen. At block 704, a hydrophobic material is selected. The hydrophobic material is selected from polyurethane, cellulosic, polyvinyl chloride (PVC), silicone or combinations thereof. In an example, polyurethane is selected. At block 706, a solvent is selected. The solvent is selected from tetrahydrofuran (THF), dimethylformamide (DMF), dimethylacetamide (DMAc), ethanol, or combinations thereof. In an example, THF is selected. At block 708, the NO release compound is selected from S-nitrosothiol, NONOate, L-arginine, nitrovasodilator, or combinations thereof. In an example, SNAP is selected. At block 710, the hydrophilic material, hydrophobic material, solvent and NO release compound are mixed together in a desired ratio. The ratio of SNAP to PVP may be in the range of about 250 to 1 to about 1 to 10. The composition may result in a gel. The amount of solvent may be adjusted to change the ratio of solvent to control the viscosity of the gel.

In an embodiment with SNAP as the NO release compound and PVP as the hydrophilic material, the SNAP cooperates with PVP to enable a particularly steady and extended NO release of the composition. In some embodiments, the composition may be formulated as follows where the formulations are percentages by weight for a total of 100%:
 a) Hydrophilic material (PVP) - 5-25%;
 b) Hydrophobic material (polyurethane) - 40-90%;
 c) NO release compound (SNAP) - up to 50% of total weight.

Figure 8:
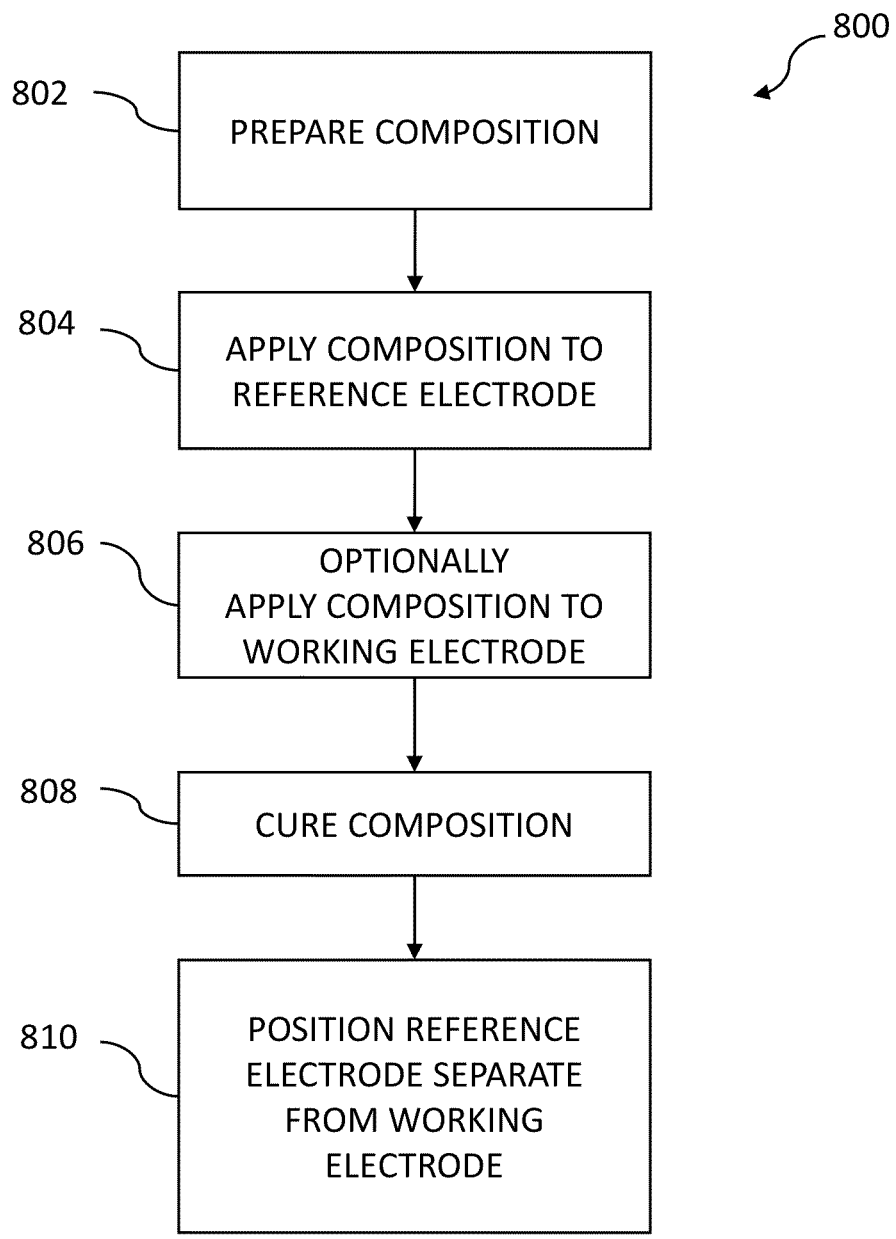
FIG. 8 is a flowchart of a method for making a subcutaneous sensor for use with a continuous glucose monitor, in accordance with some embodiments.

FIG. 8 is a flowchart of a method 800 for making a subcutaneous sensor for use with a continuous glucose monitor, in accordance with some embodiments. The method 800 starts at block 802 where a composition for releasing NO is prepared. This is described in FIG. 7, and includes mixing the hydrophilic material, hydrophobic material, solvent and NO release compound to form the composition. At block 804, the composition is applied to the reference electrode. The composition for releasing NO may be applied to the ion limiting layer, the paste, between the paste and the ion limiting layer, over the ion limiting layer forming the reference outer layer, or combinations thereof. In some embodiments, the applying the composition is by blending the composition into an ion limiting layer of the reference electrode. In some embodiments, the applying the composition forms a reference outer layer over an ion limiting layer of the reference electrode. In some embodiments, the applying the composition is by blending the composition into an ion limiting layer of the reference electrode, and the applying the composition also forms a reference outer layer over the ion limiting layer of the reference electrode. In some embodiments, the composition is part of a paste over an ion limiting layer of the reference electrode, between the paste and the ion limiting layer of the reference electrode, or part of the paste and between the paste and the ion limiting layer of the reference electrode.

The composition may be dipped, sprayed, deposited or printed using various manufacturing processes. In some embodiments, the reference wire of the reference electrode may be dip coated multiple times at room temperature and pressure. In some embodiments, the relative humidity is controlled to be between 5-20% to maintain proper viscosity.

Optionally, at block 806, the composition is applied to the working electrode. The composition for releasing NO may be applied to the glucose limiting layer, over the glucose limiting layer forming the working outer layer, or combinations thereof.

At block 808, the composition is cured to form the releasing NO on the reference electrode and optionally, on the working electrode. The composition is cured by ambient air, forcing airflow, applying heat, or applying vacuum. In one example, the curing is done at 40-60° C. for 10-30 minutes. It will be understood that other processes may be used to either speed or slow the curing process. As the composition cures, the hydrophobic and hydrophilic physically crosslink, and in particular, form hydrogen bonds. The resulting hydrogen bonded layer enables a highly desirable uniform and even passage of glucose molecules as compared to prior art chemically bonded layers. Physically crosslinking means that the polymers are crosslinked through non-covalent bonding, such as hydrogen bonding or hydrophobic interaction between two polymers in the formulation. For example, in some embodiments physical crosslinking is in the form of hydrogen bonding between polyurethane and a water-soluble polymer. Strong and resilient hydrogen-bonded structures are formed. At block 810, the reference electrode is positioned separate from the working electrode in the sensor.

The embodiments herein enable an extended release NO function that acts to provide a steady rate of NO release over an extended time. This results in the body of the patient having a slowed and reduced immune response to the in-vivo working electrode of the sensor. In this way, the sensor, such as a CGM sensor, may comfortably remain in the body of the patient for 14-21 days or more, without rejection by the body's immune system, while maintaining good stability and sensitivity. For example, the sensor may maintain biocompatibility with the patient for at least 7 days, at least 14 days or at least 21 days. In this way, the user does not need to move the CGM senser as often, reducing the number of painful insertions. Further, the disclosed NO release compounds and structures have been found to greatly reduce the interference of the NO release compound with the sensor accuracy or sensitivity.

While the specification has been described in detail with respect to specific embodiments of the invention, it will be appreciated that those skilled in the art, upon attaining an understanding of the foregoing, may readily conceive of alterations to, variations of, and equivalents to these embodiments. These and other modifications and variations to the present invention may be practiced by those of ordinary skill in the art, without departing from the scope of the present invention, which is more particularly set forth in the appended claims. Furthermore, those of ordinary skill in the art will appreciate that the foregoing description is by way of example only and is not intended to limit the invention.

What is claimed is:

1. A subcutaneous sensor for use with a continuous glucose monitor comprising:
   i) a reference electrode comprising:
      a reference substrate;
      an ion limiting layer over the reference substrate;
   ii) a working electrode comprising:
      a conductive substrate;
      an interference layer over the conductive substrate;
      an enzyme layer over the interference layer, the enzyme layer comprising an enzyme for reacting with in-vivo glucose in body fluid of a patient;
      a glucose limiting layer over the enzyme layer that limits an amount of the in-vivo glucose from the body fluid of the patient that passes to the enzyme layer; and
   iii) a composition for releasing nitric oxide (NO) comprising:
      a NO release compound;
      a hydrophilic material;
      a hydrophobic material;
      wherein the composition is on the reference electrode.

2. The subcutaneous sensor of claim 1, wherein the ion limiting layer of the reference electrode is selected from polyurethane, cellulosic, polyvinyl chloride (PVC) or combinations thereof.

3. The subcutaneous sensor of claim 1, wherein the NO release compound of the composition is selected from S-nitrosothiol, NONOate, L-arginine, nitrovasodilator or combinations thereof.

4. The subcutaneous sensor of claim 1, wherein the hydrophilic material of the composition is selected from polyvinylpyrrolidone (PVP), polyvinyl alcohol, polyacrylic acid, polyethylene oxide (PEO), silane-PEO (Si-PEO), PEO compounds, polyethylene glycol (PEG), or combinations thereof.

5. The subcutaneous sensor of claim 1, wherein the hydrophobic material of the composition is selected from polyurethane, cellulosic, polyvinyl chloride (PVC), silicone or combinations thereof.

6. The subcutaneous sensor of claim 1, wherein the composition is part of the ion limiting layer of the reference electrode.

7. The subcutaneous sensor of claim 1, wherein the composition is a reference outer layer over the ion limiting layer of the reference electrode.

8. The subcutaneous sensor of claim 1, wherein the composition is part of the ion limiting layer and a reference outer layer over the ion limiting layer.

9. The subcutaneous sensor of claim 1, further comprising a paste over the reference substrate, wherein the composition is part of the paste, between the paste and the ion limiting layer, or part of the paste and between the paste and the ion limiting layer.

10. The subcutaneous sensor of claim 1, wherein the working electrode further comprises a working outer layer over the glucose limiting layer comprising the composition for releasing the NO, the NO release compound of the composition being S-nitroso-N-acetylpenicillamine (SNAP), the hydrophilic material of the composition being polyvinylpyrrolidone (PVP), and the hydrophobic material of the composition being polyurethane.

11. The subcutaneous sensor of claim 1, wherein the glucose limiting layer of the working electrode further comprises the composition for releasing the NO, the NO release compound of the composition being S-nitroso-N-acetylpenicillamine (SNAP), the hydrophilic material of the composition being polyvinylpyrrolidone (PVP), and the hydrophobic material of the composition being polyurethane.

12. A method of making a subcutaneous sensor for use with a continuous glucose monitor comprising:
   preparing a composition for releasing nitric oxide (NO) comprising mixing a nitric oxide (NO) release compound, a hydrophilic material, a hydrophobic material, and a solvent to form a composition;
   applying the composition to a reference electrode;
   curing the composition to form the releasing NO on the reference electrode; and
   positioning the reference electrode separate from a working electrode.

13. The method of claim 12, wherein:
   the NO release compound of the composition comprises S-nitroso-N-acetylpenicillamine (SNAP);
   the hydrophilic material of the composition comprises polyvinylpyrrolidone (PVP);
   the hydrophobic material of the composition comprises polyurethane; and
   the solvent of the composition is selected from tetrahydrofuran (THF), dimethylformamide (DMF), dimethylacetamide (DMAc), ethanol, or combinations thereof.

14. The method of claim 12, wherein the applying the composition is by blending the composition into an ion limiting layer of the reference electrode.

15. The method of claim 12, wherein the applying the composition forms a reference outer layer over an ion limiting layer of the reference electrode.

16. The method of claim 12, wherein the applying the composition is by blending the composition into an ion limiting layer of the reference electrode, and the applying the composition also forms a reference outer layer over the ion limiting layer of the reference electrode.

17. The method of claim 12, wherein the composition is part of a paste over an ion limiting layer of the reference electrode, between the paste and the ion limiting layer of the reference electrode, or part of the paste and between the paste and the ion limiting layer of the reference electrode.

18. The method of claim 12, wherein the working electrode comprises:
   a conductive substrate;
   an interference layer over the conductive substrate;
   an enzyme layer over the interference layer and comprising an enzyme for reacting with in-vivo glucose in body fluid of a patient; and
   a glucose limiting layer over the enzyme layer that limits an amount of the in-vivo glucose from the body fluid of the patient that passes to the enzyme layer.

19. The method of claim 18, further comprising applying the composition for releasing the NO over the glucose limiting layer forming a working outer layer, the NO release compound of the composition being S-nitroso-N-acetylpenicillamine (SNAP), the hydrophilic material of the composition being polyvinylpyrrolidone (PVP), and the hydrophobic material of the composition being polyurethane.

20. The method of claim 18, further comprising mixing the composition for releasing the NO into the glucose limiting layer, the NO release compound of the composition being S-nitroso-N-acetylpenicillamine (SNAP), the hydrophilic material of the composition being polyvinylpyrrolidone (PVP), and the hydrophobic material of the composition being polyurethane.

* * * * *